Nov. 29, 1960 O. L. WEEKS Plant Pat. 1,990
ROSE PLANT
Filed Feb. 24, 1960
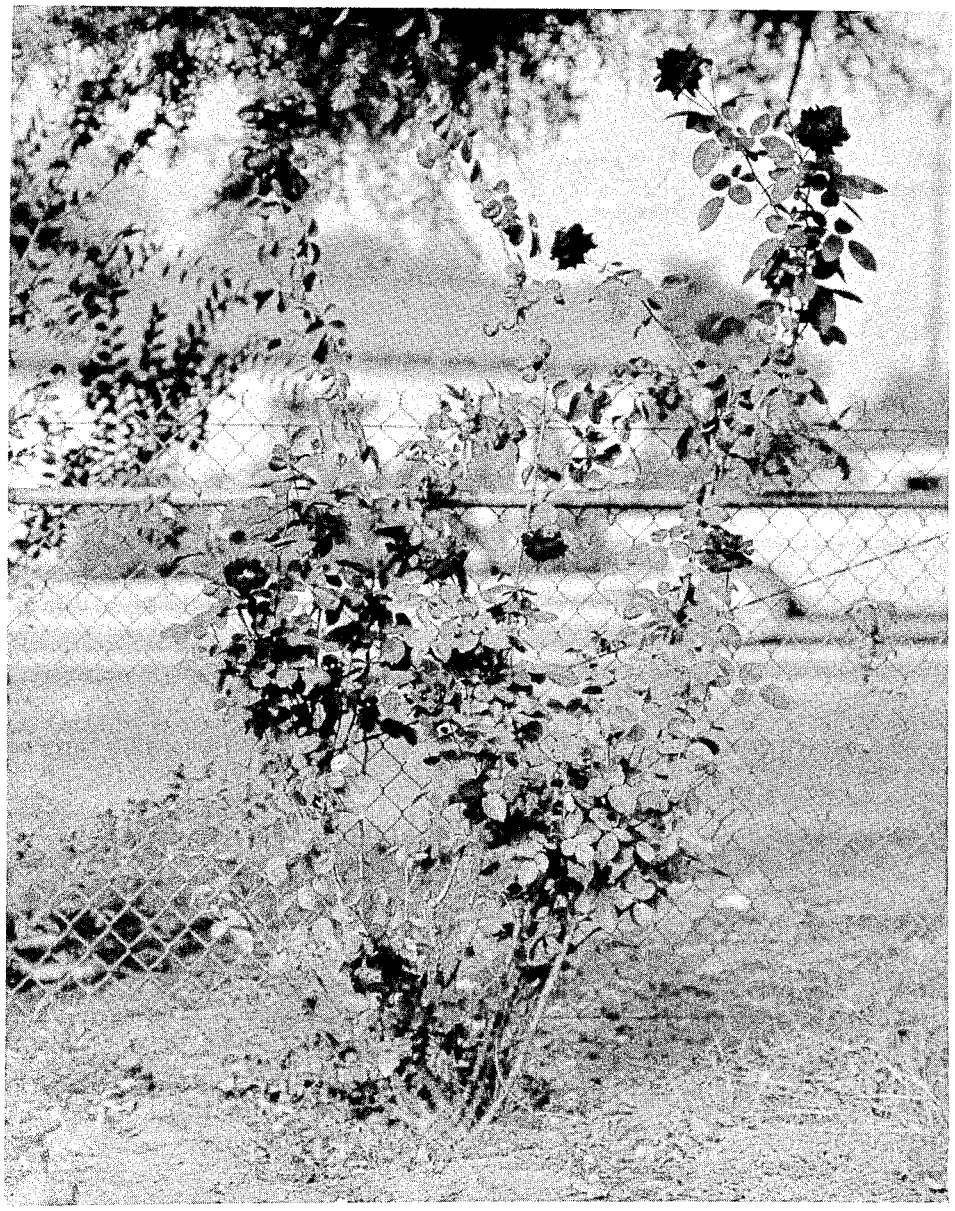
INVENTOR
O. L. Weeks
BY Robb & Robb
ATTORNEYS United States Patent Office Plant Pat. 1,990
Patented Nov. 29, 1960

1,990

ROSE PLANT

O. L. Weeks, Chino, Calif., assignor to Constance A. Elmer, trading as Elmer Roses, San Gabriel, Calif.

Filed Feb. 24, 1960, Ser. No. 10,823

1 Claim. (Cl. 47—61)

The present invention relates to a new and distinct variety of rose plant of the climbing floribunda class, which was discovered by me as a sport of the variety known as "Carrousel" (Plant Patent No. 1,066).

The new sport was initially discovered by me in a stool block of rose plants of the variety "Carrousel" which were being grown under my personal supervision and control on property being leased by me as part of my commercial nursery operations at Ontario, California. During my cultivation of the plants of the parent variety "Carrousel," my attention was attracted to one particular plant which exhibited a climbing habit as distinguished from the normal bush habit of growth of "Carrousel." Upon closer examination of this plant, I found that it had sported and I thereupon took steps to preserve the sport, keep it under observation, and later to asexually reproduce the same.

Continued observations of the original sport and the asexual reproductions thereof, as made by me by budding in my fields at Ontario, California, fully confirmed the climbing habit of the new sport, and conclusively established that this climbing habit comes true to form and is transmissible through succeeding propagations.

The climbing habit of the new variety aforesaid is evidenced by long canes which attain a height of from 10 to 16 feet. Excepting for the climbing habit, the new variety is substantially identical to its parent "Carrousel" from the standpoint of both the flows and foliage. So far as I am aware, the parent variety "Carrousel" has never exhibited a climbing habit and its growth has been that of the average bush type large flowered floribunda rose, while the new sport is definitely differentiated therefrom by its vigorous and upright climbing habit.

The accompanying drawing shows a specimen plant of the new variety which is illustrative of its typical climbing habit of growth.

In view of the similarities in general characteristics between the new variety and its parent "Carrousel," excepting for the aforementioned climbing habit of the new variety, it is unnecessary to described the new variety in further detail. The other details may be ascertained and confirmed by reference to Plant Patent No. 1,066, dated January 15, 1952, to which access may be readily had.

I claim:

A new and distinct variety of rose plant of the climbing floribunda class, substantially as herein shown and described, characterized particularly as to novelty by its general similarity to its parent variety "Carrousel" (Plant Patent No. 1,066), but being principally distinguished therefrom by its vigorous and upright climbing habit.

No references cited.